United States Patent
Tadokoro et al.

(10) Patent No.: US 7,154,108 B2
(45) Date of Patent: Dec. 26, 2006

(54) PARTICLE THERAPY SYSTEM

(75) Inventors: Masahiro Tadokoro, Hitachiohta (JP); Shunji Kakiuchi, Mito (JP); Hiroshi Akiyama, Hitachiohta (JP); Mamoru Katane, Hitachi (JP); Koji Matsuda, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/128,195

(22) Filed: May 13, 2005

(65) Prior Publication Data

US 2005/0205806 A1 Sep. 22, 2005

Related U.S. Application Data

(63) Continuation of application No. 10/971,004, filed on Oct. 25, 2004.

(30) Foreign Application Priority Data

Oct. 24, 2003 (JP) ............................. 2003-363992

(51) Int. Cl.
*A61N 5/00* (2006.01)

(52) U.S. Cl. ................... 250/492.3; 250/492.23

(58) Field of Classification Search ............... None
See application file for complete search history.

(56) References Cited

U.S. PATENT DOCUMENTS

| | | | | |
|---|---|---|---|---|
| 4,588,891 A | * | 5/1986 | Saito .......................... 250/310 |
| 4,937,458 A | * | 6/1990 | Fujikura ................... 250/492.2 |
| 4,990,778 A | * | 2/1991 | Norioka ...................... 250/310 |
| 5,449,915 A | * | 9/1995 | Yamada et al. ............. 250/397 |
| 5,969,355 A | * | 10/1999 | Fujii et al. .................. 250/309 |
| 6,034,377 A | | 3/2000 | Pu | |
| 6,207,952 B1 | | 3/2001 | Kan et al. | |
| 6,316,776 B1 | | 11/2001 | Hiramoto et al. | |
| 6,555,830 B1 | * | 4/2003 | Mankos et al. .......... 250/492.2 |
| 2004/0179648 A1 | * | 9/2004 | Svatos ......................... 378/65 |

FOREIGN PATENT DOCUMENTS

| JP | 11-64530 | 3/1999 |
|---|---|---|
| JP | 2000-202047 | 7/2000 |

OTHER PUBLICATIONS

"Light-Ion Beams for Cancer"J Review of Scientific Instruments, vol. 64, No. 8, pp. 2076-2086 (Aug. 1993).

(Continued)

*Primary Examiner*—Nikita Wells
*Assistant Examiner*—Anthony Quash
(74) *Attorney, Agent, or Firm*—Dickstein Shapiro LLP

(57) ABSTRACT

A particle therapy system capable of measuring energy of a charged particle beam even during irradiation of the charged particle beam is provided. A beam delivery (irradiation) system comprises a block collimator constituted by a pair of collimator members, and an energy detector mounted to one of the collimator members to be disposed on the upstream side thereof. When the pair of collimator members are moved in directions away from each other, a beam passage is formed between them. The energy detector constitutes an energy measuring device together with a signal processing unit. A part of the ion beam having reached the interior of the irradiation nozzle is irradiated to a patient through the beam passage. When a part of the remaining ion beam enters the energy detector, electric charges generate in the energy detector. The signal processing unit determines energy of the ion beam based on a position within the energy detector at which electric charges have generated in maximum amount.

6 Claims, 4 Drawing Sheets

OTHER PUBLICATIONS

Gottschalk et al., "Nuclear Interactions of 160 MeV Protons Stopping in Copper: A Test of Monte Carlo Nuclear Models" Med. Phys. 26 (12), pp. 2597-2601 (Dec. 1999).

G. Coutrakon et al., "A beam intensity monitor for the Loma Linda cancer therapy proton accelerator," Med. Phys. 18(4), Jul./Aug. 1991, pp. 817-820.

D.W. Litzenberg et al., "On-line monitoring of radiotherapy beams: Experimental results with proton beams," Med. Phys. 26(6), Jun. 1999, pp. 992-1006.

Eros Pedroni et al., "The 200-MeV proton therapy project at the Paul Scherrer Institute: Conceptual design and practical realization," Medical Physics, vol. 22, No. 1, Jan. 1995, pp. 37-53.

W.T. Chu, "Instrumentation in Medical Systems," Lawrence Berkeley Laboratory, University of California, Berkeley, CA 94720, 1996 IEEE, pp. 2394-2398.

Bernard Gottschalk et al., "Nuclear interactions of 160 MeV protons stopping in copper: A test of Monte Carlo nuclear models," Med. Phys. 26(12), Dec. 1999, pp. 2597-2601.

* cited by examiner

PARTICLE THERAPY SYSTEM

CROSS-REFERENCE TO RELATED APPLICATION

This application is a continuation of U.S. patent application Ser. No. 10/971,004, filed on Oct. 25, 2004, the subject matter of which is incorporated in its entirety by reference herein.

BACKGROUND OF THE INVENTION

1. Field of the Invention

The present invention relates to a particle beam irradiation apparatus for use in medical treatment to accelerate and irradiate a particle beam. The present invention also relates to a safety device for the particle beam irradiation apparatus.

2. Description of the Related Art

In a particle therapy system, an accelerator accelerates a charged particle beam, i.e., a particle beam (such as a proton beam or a heavy charged-particle beam (e.g., a carbon ion beam)), and the accelerated charged particle beam is used for treatment of cancers (diseased parts). The particle therapy system includes an irradiation nozzle for irradiating the charged particle beam to a cancer. The particle beam will be referred to as an "ion beam" hereinafter. The irradiation nozzle spreads the ion beam in match with the cancer in a direction perpendicular to the direction of advance of the ion beam. This process is called spread of an irradiation field. For the spread of the irradiation field, there are known a scattering method (see Non-Patent Reference 1; "REVIEW OF SCIENTIFIC INSTRUMENTS", Vol. 64, No. 8 (August 1993), pp. 2076–2086), and a wobbling method (see Patent Reference 1; JP,A 2000- 202047, and Non-Patent Reference 1). According to the scattering method, a scatterer is installed in a beam path within the irradiation nozzle to enlarge the ion beam through scattering by the scatterer. According to the wobbling method, a pair of scanning magnets provided in the irradiation nozzle are energized to scan the ion beam so as to draw a circle, thereby spreading the ion beam. In some cases, both the scattering method and the wobbling method are used in a combined manner. The irradiation nozzle further includes a SOPB (spread-out of Bragg peak) device (e.g., a ridge filter or a range modulation wheel) for spreading out an energy distribution to increase the range in the direction of advance of the ion beam, a fine degrader for adjusting the energy of the ion beam to final irradiation energy, a collimator for cutting the ion beam that is not necessary for the irradiation, a dose monitor, and a beam position monitor.

The energy (namely, range) of the ion beam irradiated to the cancer can be measured by a water phantom device (see Patent Reference 2; JP,A 11-64530) attached in the irradiation nozzle. As another method, the energy of the ion beam can also be measured by laminating metallic plates and detecting, from each of the metallic plates, the amount of charges lost through the metallic plates when the ion beam passes them.

SUMMARY OF THE INVENTION

When measuring the energy of the ion beam by the water phantom device, the water phantom device has hitherto been arranged in the beam path within the irradiation nozzle before start of the cancer treatment. After end of the energy measurement, the water phantom device is moved away from the beam path so as not to interfere with the ion beam used for the treatment. With the related art thus constructed, the energy of the ion beam cannot be measured during a period in which the treatment is performed under irradiation of the ion beam.

It is an object of the present invention to provide a particle therapy system capable of measuring energy of a charged particle beam even during irradiation of the charged particle beam.

To achieve the above object, according to the particle therapy system of the present invention, a charged particle beam irradiation apparatus comprises a collimator for passing a part of a charged particle beam therethrough, and an energy measuring device including a charged particle beam entrance portion disposed upstream of the collimator to receive at least a part of the remaining charged particle beam, for measuring energy of the charged particle beam having entered the charged particle beam entrance portion.

With the present invention, since a part of the charged particle beam blocked off by the collimator is caused to enter the charged particle beam entrance portion for detection of the energy of the charged particle beam, the energy of the charged particle beam can be measured while the charged particle beam having passed a beam passage formed by the collimator is irradiated to an irradiation target (e.g., a patient).

Preferably, the charged particle beam entrance portion disposed upstream of the collimator is mounted to the collimator. With this arrangement, the charged particle beam entrance portion and the collimator can be moved together, and therefore the structure of the charged particle beam irradiation apparatus can be simplified.

Preferably, the particle therapy system further comprises a safety device for stopping extraction of the charged particle beam from a charged particle beam generation apparatus when a measured energy value of the charged particle beam measured by the energy measuring device exceeds a setting energy value. During a period in which the charged particle beam is irradiated to the irradiation target, even if the energy of the charged particle beam should varies, the irradiation of the charged particle beam to the irradiation target can be immediately stopped with the function of the safety device. If the charged particle beam having energy changed from the setting energy value is irradiated to the irradiation target, the irradiation position of the charged particle beam in a direction of depth from an entrance surface of the irradiation target is deviated from the predetermined position (i.e., the irradiation position set in a treatment plan). The provision of the safety device can prevent the charged particle beam from being irradiated to the irradiation position different from the predetermined one.

Preferably, upstream of the charged particle beam entrance portion, an energy attenuating device is disposed which is movable in a direction intersecting a beam path along which the charged particle beam passes, and which attenuates the energy of the charged particle beam having entered the charged particle beam entrance portion. The energy measuring device compensates a measured energy value of the charged particle beam having entered the charged particle beam entrance portion based on a value by which the energy of the charged particle beam has attenuated through the energy attenuating device. As a result, the energy of the charged particle beam having high energy can be measured with high accuracy by employing the charged particle beam entrance portion that has a relatively small thickness in the direction of advance of the charged particle beam. Since the thickness of the charged particle beam entrance portion in the direction of advance of the charged particle beam is reduced, the length of the charged particle beam irradiation apparatus in the direction of advance of the charged particle beam can be reduced as compared with the case not employing the energy attenuating device.

According to the present invention, the energy of the charged particle beam can be measured while continuing the irradiation of the charged particle beam.

DESCRIPTION OF THE PREFERRED EMBODIMENTS

Figure 1:
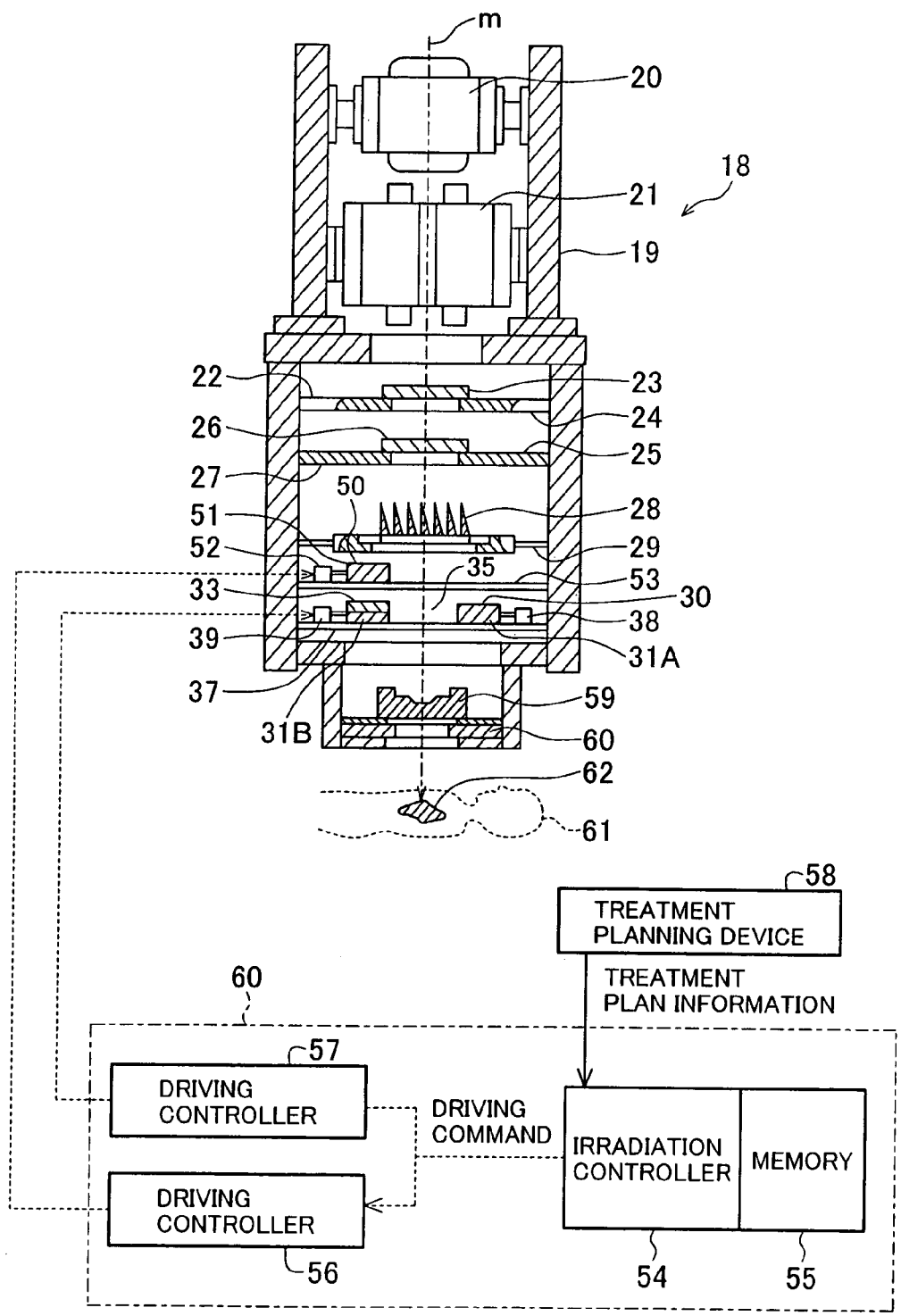
FIG. 1 is a vertical sectional view of a particle therapy system in a particle therapy system according to one preferable embodiment of the present invention.
Figure 2:
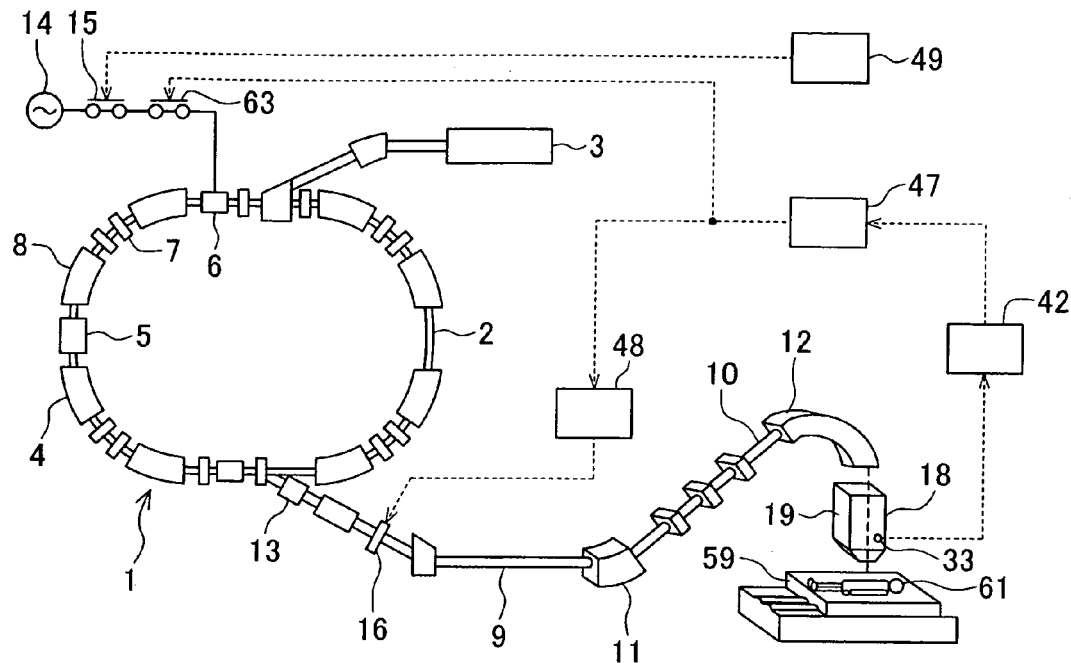
FIG. 2 is a schematic view of the particle therapy system according to one preferable embodiment of the present invention.

A particle therapy system according to one embodiment of the present invention will be described below with reference to FIGS. 1 and 2.

A particle therapy system 1 of this embodiment comprises a charged particle beam generation apparatus 2 and an irradiation nozzle (charged particle beam irradiation apparatus) 18. The charged particle beam generation apparatus 2 comprises an ion source (not shown), a pre-accelerator 3, and a synchrotron 4. Ions (e.g., protons or carbon ions) generated by the ion source are accelerated by the pre-accelerator (e.g., a linear accelerator) 3. This embodiment is practiced as a proton beam therapy system using a proton beam as an ion beam. The ion beam emitted from the pre-accelerator 3 enters the synchrotron 4. The ion beam is accelerated in the synchrotron 4 serving as an accelerator in which it is given with energy by radio-frequency (RF) power applied from an RF cavity 5. After energy of the ion beam circulating in the synchrotron 4 has increased up to a setting level, a switch 15 is closed in accordance with an extraction command from an accelerator controller 49. Correspondingly, RF power from an RF power supply 14 is applied to an RF knockout electrode 6 through the switch 15, and an RF wave is applied to the circulating ion beam from the RF knockout electrode 6. During the process described above, a switch 63 is kept closed. With the application of the RF wave, the ion beam circulating in the synchrotron 4 within a separatrix is forced to transit to the outside of the separatrix and to exit from the synchrotron 4 through an extraction deflector 13. At the time of extracting the ion beam, currents supplied to magnets, such as quadrupole magnets 7 and bending magnets 8, disposed in the synchrotron 4 are held at respective setting values, and therefore the separatrix is also held substantially constant. The extraction of the ion beam from the synchrotron 4 is stopped by opening the switch 15 in accordance with an extraction stop command from accelerator controller 49 and ceasing the application of the RF power to the RF knockout electrode 6.

The ion beam extracted from the synchrotron 4 reaches the irradiation nozzle 18, serving as the irradiation apparatus, through a beam transportation line 9. An inverted U-shaped section 10 as a part of the beam transportation line 9 and the irradiation nozzle 18 are both mounted on a rotating gantry (not shown). The inverted U-shaped section 10 includes bending magnets 11, 12. The ion beam is irradiated from the irradiation nozzle 18 to a cancer (diseased part) 62 (FIG. 1) in the body of a patient 61 lying on a treatment couch (bed) 59. A shutter 16 opened and closed by a driving unit 17 is disposed in the beam transportation line 9. The shutter 16 is kept open while the ion beam is irradiated to the cancer 62 from the irradiation nozzle 18.

The detailed structure of the irradiation nozzle 18 used in this embodiment will be described below with reference to FIG. 1. The irradiation nozzle 18 is a wobbling type system. The irradiation nozzle 18 has a casing 19 mounted to the inverted U-shaped section 10. Within the casing 19, the following units are arranged successively from the upstream side in the direction of advance of the ion beam, i.e., scanning magnets 20, 21, a scatterer device 22, a range adjuster 25, a device for spreading out the Bragg peak (referred to as an "SOBP device" hereinafter) 28, a beam energy attenuating device 50, a block collimator 30, a bolus 59, and a patient collimator 60. An energy detector 33 (see FIG. 3) is disposed upstream of the block collimator 30 and is mounted to the block collimator 30. The scanning magnets 20, 21 are mounted to the casing 19 upstream of the scatterer device 22. The scatterer device 22 includes a scatterer 23 attached to a support member 24 having an opening. The support member 24 is mounted to the casing 19. The range adjuster 25 comprises an absorber 26 and a support member 27 for holding the absorber 26 with respect to the casing 19. A ridge filter and a rotating range modulation wheel are known as examples of the SOBP device 28. In this embodiment, the ridge filter is used as the SOBP device 28. The SOBP device 28 is held by a support member 29 which is mounted to the casing 19.

Figure 3:
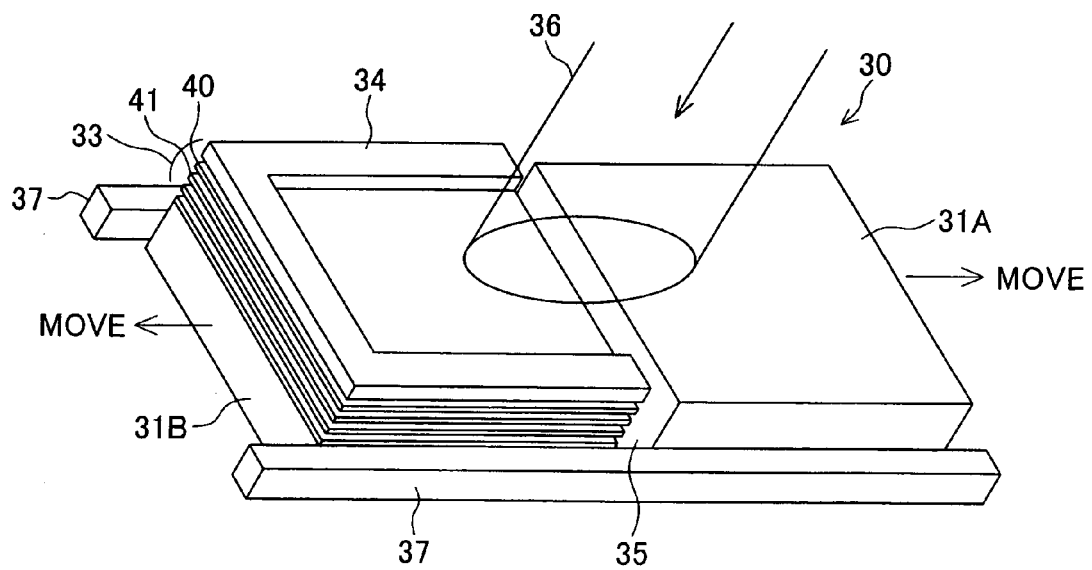
FIG. 3 is a perspective view of a block collimator and an energy detector both shown in FIG. 1.

The structure of the block collimator 30 and the energy detector 33 will be described below with reference to FIG. 3. The block collimator 30 comprises a pair of collimator members 31A, 31B. The collimator members 31A, 31B are each made of a radiation shield material, e.g., lead or tungsten, capable of blocking off the ion beam. The collimator members 31A, 31B are movably mounted to a pair of linear guides 37 disposed within the casing 19 in horizontally intersecting relation. The pair of linear guides 37 are arranged with a space left between them so as not to interfere with the ion beam, and are fixedly mounted to an inner surface of the casing 19. A driving unit 38 is disposed at an end of one of the linear guides 37, and a driving unit 39 is disposed at an end of the other linear guide 37. The driving unit 38 is coupled to the collimator member 31A, and the driving unit 39 is coupled to the collimator member 31B. With operations of the driving units 38, 39, the collimator members 31A, 31B are moved in opposite directions (i.e., in directions approaching each other or directions away from each other) along the linear guides 37. When the collimator members 31A, 31B are moved in the directions away from each other, a space formed between the collimator members 31A, 31B, i.e., a beam passage 35, is increased. Conversely, when the collimator members 31A, 31B are moved in the directions approaching each other, the beam passage 35 is narrowed. The width of the beam passage 35 is adjusted depending on the size of the cancer 62.

Figure 4:
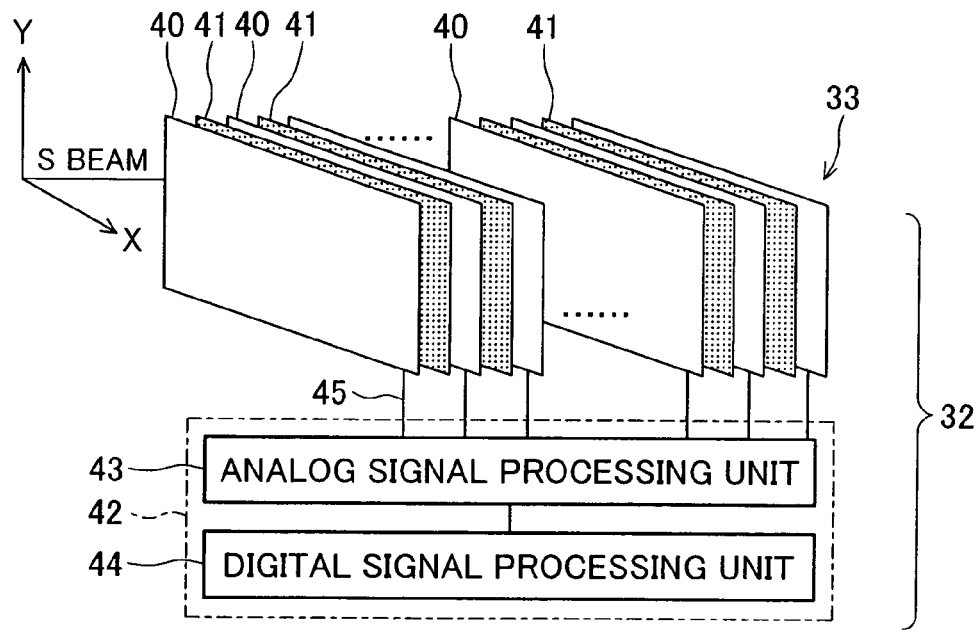
FIG. 4 shows a structure of an energy measuring device.

An energy measuring device 32 comprises the energy detector 33 and a signal processing unit 42 (see FIG. 4). As shown in FIGS. 3 and 4, the energy detector 33 is of a structure comprising many thin copper sheets (electrodes) 40 and polyimide films 41 which are alternately arranged in parallel. For example, the energy detector 33 is constituted by arranging eighty copper sheets 40 each having a thickness of 0.15 mm side by side in the direction of advance of the ion beam. Each copper sheet 40 serves as an energy sensor. The copper sheets 40 and the polyimide films 41 thus arranged are detachably fixed to the collimator member 31B by attaching a retainer 34 to the collimator member 31B with screws (not shown). Polyimide is an electrically insulating material, and each polyimide film 41 serves to prevent electrical connection between adjacent two of the copper sheets 40. Because the copper sheets 40 of the energy detector 33 have the function of attenuating the energy of the ion beam, the thickness of the collimator member 31B is set to be smaller than that of the collimator member 31A. Even if some of the ion beam passes through the energy detector 33, it can be completed blocked off by the collimator member 31B which is disposed downstream of the energy detector 33.

As shown in FIG. 4, the signal processing unit 42 comprises an analog signal processing unit 43 and a digital signal processing unit 44. The copper sheets 40 are connected to the analog signal processing unit 43 by respective wires 45. The analog signal processing unit 43 has individual amplifiers (not shown) in one-to-one relation to the copper sheets 40. The wires 45 connect the copper sheets 40 to the corresponding amplifiers. The amplifiers are each connected to the digital signal processing unit 44.

This embodiment includes a control system 60 comprising an irradiation controller 54, a memory 55, and driving controllers 56, 57. The control system 60 further comprises a driving controller (not shown) for controlling respective movements of the scatterer 23 and the absorber 26 which are described later in more detail. As shown in FIG. 2, the signal processing unit 42 (specifically the digital signal processing unit 44) is connected to an interlock device 47 serving as a safety device. The interlock device 47 is connected to a shutter controller 48 and the switch 63.

The beam energy attenuating device 50 comprises an energy attenuator 51 made of copper and a driving unit 52. The energy attenuator 51 is movable along a guide member 53 extending in a direction perpendicular to the direction of advance of the ion beam. The guide member 53 is mounted to the inner surface of the casing 19. The thickness of the energy attenuator 51 is much larger than that of the copper sheet 40.

Prior to positioning of a patient 61 relative to the irradiation nozzle 18, the irradiation controller 54 receives treatment plan information for the patient 61 (such as an irradiation field size (irradiation field information), a range (range information) and incident energy (beam energy information)) from a treatment planning device 58, and then stores the received data in the memory 55. The treatment plan information represents conditions for irradiating the ion beam. In accordance with the treatment plan information, the irradiation controller 54 selects the scatterer 23 and the absorber 26 each having a thickness required to meet the irradiation conditions. As the incident energy of the ion beam increases, the scatterer 23 having a larger thickness is selected, and as the required range decreases, the absorber 26 having a larger thickness is selected. Respective driving controllers (not shown) move the selected scatterer 23 and absorber 26 to a beam path (beam axis m) in the casing 19. The scatterer 23 and the absorber 26 are thus positioned to lie on the beam axis m.

Figure 5:
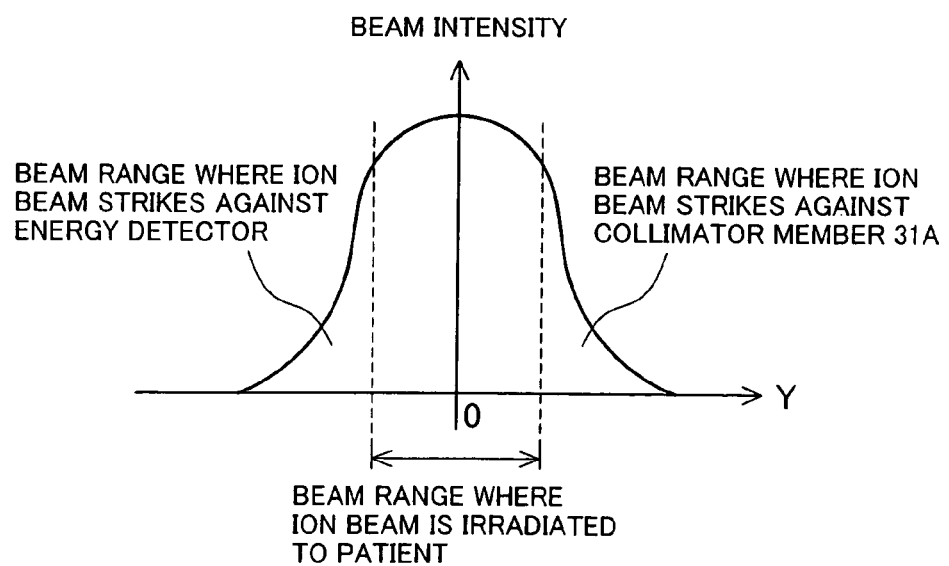
FIG. 5 is a graph for explaining a distribution of intensity of an ion beam immediately before the ion beam enters the block collimator, and respective ranges of the ion beams entering the energy detector, a beam passage, and a collimator member.

Further, in accordance with the irradiation field information, the irradiation controller 54 outputs a first movement command for the collimator members 31A, 31B to the driving controller 57. The driving controller 57 operates the driving units 38, 39 in accordance with the first movement command such that the collimator members 31A, 31B are moved to respective predetermined positions. At this time, the beam passage 35 formed between the collimator members 31A, 31B has a width corresponding to the irradiation field size set for the patient 61. The energy detector 33 is also moved together with the collimator member 31B to reach a predetermined position (i.e., a position where the energy detector 33 intersects a part of an ion beam passing area which is located on the left side of a left broken line shown in FIG. 5). When the incident energy of the ion beam entering the patient 61 exceeds a setting level, the irradiation controller 54 outputs a second movement command to the driving controller 56. The driving controller 56 operates the driving unit 52 in accordance with the second movement command such that the energy attenuator 51 is moved along the guide member 53 to a predetermined position where it intersects a portion of the beam path. As a result, the energy attenuator 51 is moved to a position where it overlies the energy detector 33 in exactly aligned relation without projecting into the beam passage 35. When the incident energy of the ion beam is less than the setting level, the driving unit 52 is not operated and the energy attenuator 51 is held in a position where it does not overlap with the energy detector 33. To prevent the incident energy of the ion beam irradiated to the patient 61 under the treatment from exceeding the setting level, the energy attenuator 51 must be positioned in exactly aligned relation to the energy detector 33.

Then, a rotating gantry is rotated to make the beam axis m of the irradiation nozzle 18 oriented at a predetermined angle. With that positioning, the beam axis m of the irradiation nozzle 18 is aligned with the cancer 62 in the body of the patient 61. The preparations for irradiating the ion beam to the patient 61 are thereby completed. Subsequently, as described above, the ion beam having entered the synchrotron 4 from the pre-accelerator 3 is caused to exit from the synchrotron 4 and reach the irradiation nozzle 18. At this time, the shutter 16 is in the open state.

In the irradiation nozzle 18, the ion beam is spread out by the scatterer 23 in the direction perpendicular to the beam axis m, and the range of the ion beam is adjusted by the absorber 26. Further, the ion beam passes through the SOBP device 28 and reaches above the block collimator 30. At this time, the ion beam is spread out as indicated by 36 in FIG. 3. A part of the ion beam passes the beam passage 35. The ion beam having passed the beam passage 35 is irradiated to the cancer 62 after passing through the bolus 59 and the patient collimator 60. In such a way, the treatment of the cancer 62 is performed by the irradiation of the ion beam.

One part of the remaining ion beam having reached above the block collimator 30 is blocked off by the collimator member 31A, and other part thereof passes through the energy attenuator 51 and then enters the energy detector 33. The energy detector 33 detects the energy of the ion beam by receiving the ion beam that is not used for the treatment, namely that is not irradiated to the cancer. That condition will now be described in detail with reference to FIG. 5. The ion beam having passed through the SOBP device 28 has a distribution of beam intensity indicated by a solid line in a graph of FIG. 5. The ion beam locating within an area formed between a pair of broken lines in the distribution graph is irradiated to the cancer 62. The ion beam locating within an area on the right side of the right broken line in FIG. 5 strikes against the collimator member 31A and is blocked off. The ion beam (unnecessary ion beam) locating within an area on the left side of the left broken line in FIG. 5 passes through the energy attenuator 51 and then enters the energy detector 33. The energy of the ion beam is attenuated by the energy attenuator 51. An amount by which the energy of the ion beam is attenuated by the energy attenuator 51 is measured in advance and therefore it is a known value.

Figure 6:
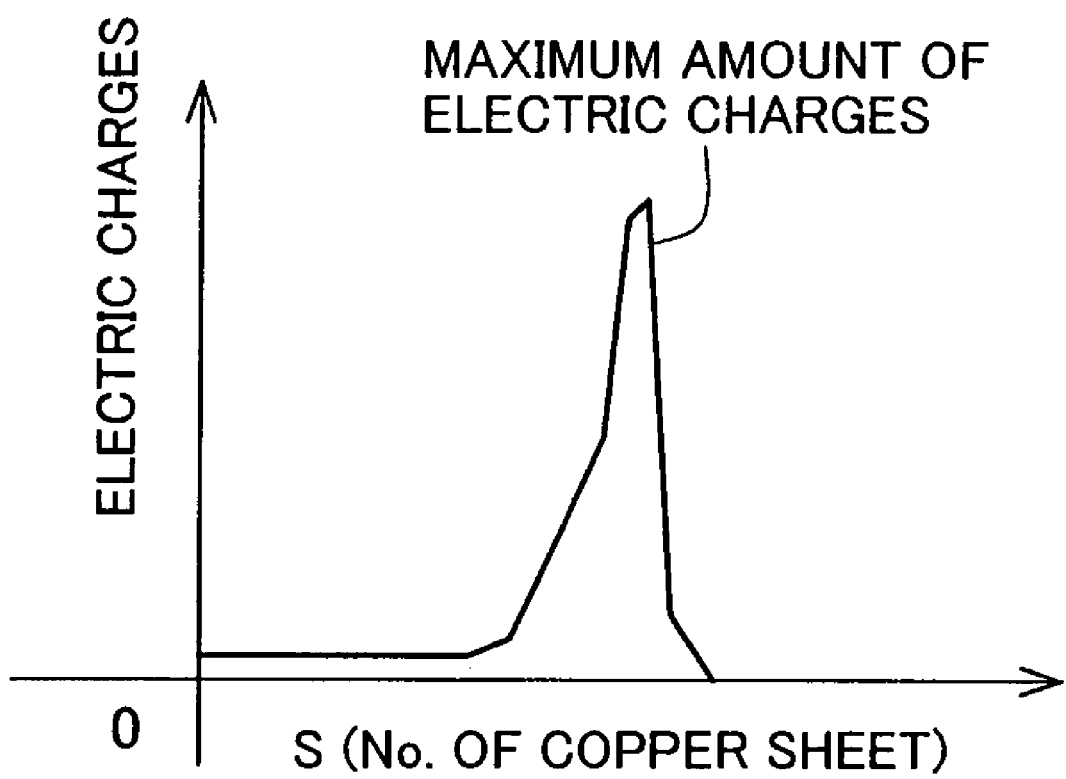
FIG. 6 is a graph showing, by way of example, the amount of electric charges outputted from each of copper sheets arranged in parallel within the energy detector.

A description is now made of the measurement of the ion beam energy by the energy detector 33. Until which one of the copper sheets 40 the ion beam having entered the energy detector 33 (i.e., the ion beam locating within the area on the left side of the left broken line in FIG. 5) reaches is determined depending on the energy of the ion beam at the time when the ion beam enters the first one of the copper sheets 40. In other words, as the incident energy of the ion beam increases, the ion beam reaches until the copper sheet 40 which is located at a deeper position in the direction of advance of the ion beam (i.e., the direction of the beam axis m) with respect to the copper sheet 40 which is located at the shallowest position. Each of the copper sheets, which are included in a zone ranging from the copper sheet 40 which the ion beam first enters to the copper sheet 40 which the ion beam finally reaches, generates electric charges corresponding to an amount of energy loss of the ion beam having entered the relevant copper sheet 40. The ion beam is stopped in the copper sheet 40 where the ion beam energy has become 0 (i.e., in one copper sheet which is located at the deepest position among the copper sheets which the ion beam has entered), while releasing a maximum amount of electric charges (see FIG. 6). Respective amounts of electric charges generated by the copper sheets 40 are amplified by the corresponding amplifiers in the analog signal processing unit 43 through the respective wires 45, and then transmitted to the digital signal processing unit 44. Based on the input amounts of electric charges, the digital signal processing unit 44 recognizes the address of the copper sheet 40 that has outputted the maximum amount of electric charges. The addresses of the copper sheets 40 mean the numbers successively assigned to the copper sheets, counting from the surface side of the energy detector 33 closer to the SOBP device 28 in the direction of advance of the ion beam. The digital signal processing unit 44 stores, in a memory (not shown), the addresses successively assigned as Nos. 1, 2, etc. to the respective copper sheets 40, starting from the surface side of the energy detector 33 closer to the SOBP device 28 in the direction of advance of the ion beam. In other words, each of the addresses represents at what number the relevant copper sheet 40 locates, counting from the surface side of the energy detector 33 closer to the SOBP device 28. The digital signal processing unit 44 searches for corresponding one of the addresses stored in the memory in accordance with a charge input point from the copper sheet 40 that has outputted the maximum amount of electric charges (i.e., the position connected to the relevant copper sheet 40), thereby recognizing the address of the copper sheet 40 that has outputted the maximum amount of electric charges. Then, the digital signal processing unit 44 determines the energy of the ion beam in accordance with the recognized address of the copper sheet 40.

The relationship between each copper sheet and the energy of the ion beam is determined in advance based on a test. More specifically, the address of the copper sheet 40 outputting the maximum amount of electric charges is confirmed by causing the ion beams having various levels of energy to enter the energy detector 33 in each of the cases where the ion beam passes through the energy attenuator 51 and where the ion beam does not pass through it. The digital signal processing unit 44 stores, in the memory, information that is obtained from the test result and represents the correspondent relationship between each energy level and the address of the copper sheet 40 outputting the maximum amount of electric charges which corresponds to each energy level. The information representing the correspondent relationship is prepared separately for each the case where the energy attenuator 51 is positioned in partly intersecting relation to the ion beam passing area and the case where the energy attenuator 51 is not so positioned. By knowing whether the energy attenuator 51 partly intersects the ion beam passing area or not and the address of the copper sheet 40 having outputted the maximum amount of electric charges when the ion beam is allowed to enter the irradiation nozzle 18, the digital signal processing unit 44 can determine the energy of the ion beam at that time based on the information representing the correspondent relationship between the energy and the address, which is stored in the memory (i.e., direct measurement of the ion beam energy). When the energy attenuator 51 is positioned in partly intersecting relation to the ion beam passing area, true energy of the ion beam can be determined by compensating the ion beam energy determined from the address of the copper sheet 40 having outputted the maximum amount of electric charges based on a value by which the ion beam energy has attenuated through the energy attenuator 51 (i.e., compensated measurement of the ion beam energy). Because the polyimide film 41 is very thin (e.g., 75 μm), there is little probability that an ion beam will stop at the position of polyimide film 41.

The digital signal processing unit 44 outputs the energy value information thus obtained to the interlock device 47 serving as the safety device. The interlock device 47 receives, from the treatment planning device 53, the beam energy information (setting energy value) for the patient 61 under the treatment by irradiation of the ion beam, and then compares the setting energy value with the energy value (measured energy value) from the digital signal processing unit 44. When the measured energy value exceeds the setting energy value, the interlock device 47 opens the switch 63. As a result, the application of RF power to the RF knockout electrode 6 is stopped, whereby the extraction of the ion beam from the synchrotron 4 is forcibly stopped. Further, when the measured energy value exceeds the setting energy value, the interlock device 47 outputs a shutter closing signal to the shutter controller 48. In response to the shutter closing signal, the shutter controller 48 closes the shutter 16.

When the measured energy value is not larger than the setting energy value, the interlock device 47 does not open the switch 63. Accordingly, the extraction of the ion beam from the synchrotron 4 is continued, and the ion beam having exited from the irradiation nozzle 18 is irradiated to the patient 61. The shutter 16 is kept in the open state.

With this embodiment, since a part of the ion beam blocked off by the block collimator 30 is caused to enter the energy detector 33 for detection of the energy of the ion beam, the ion beam energy can be measured while the ion beam having passed the beam passage 35 is irradiated to the patient 61. Also, when the ion beam energy exceeds the setting energy value during a period in which the ion beam is irradiated for the treatment of the patient 61, the extraction of the ion beam from the synchrotron 4 can be stopped. As a result, the ion beam having energy in excess of the energy setting value can be prevented from being irradiated to the patient 61.

Further, with this embodiment, since the energy detector 33 is installed on the collimator member 31B, the energy detector 33 and the collimator member 31B can be both moved by one driving unit 39. This eliminates the necessity of installing separate driving units for the energy detector 33 and the collimator member 31B, whereby the construction of the irradiation nozzle can be simplified. Since the beam energy attenuating device 50, specifically the energy attenuator 51, is positioned upstream of the energy detector 33, a detectable energy range of the ion beam can be increased by utilizing the energy attenuator 51. In other words, the energy of the ion beam having a high level of energy can also be detected. If the energy attenuator 51 were not installed, it would be required to noticeably increase not only the number of the copper sheets 40 constituting the energy detector 33, but also the number of Kapton (polyimide) films, thus resulting in a greatly increased thickness of the energy detector 33 in the direction of the beam axis m. In contrast, the provision of the beam energy attenuating device 50 can realize a great reduction in thickness of the energy detector 33 in the direction of the beam axis m.

Even when the beam energy attenuating device 50 is not installed, the ion beam energy can be measured while the ion beam is irradiated to the patient 61.

The energy detector 33 may be separated from the collimator member 31B and disposed upstream of the block collimator 30 in the casing 19. However, this case requires two driving units to be installed to individually move the energy detector 33 and the collimator member 31B.

The irradiation nozzle 18 used in the above-described embodiment is also applicable to a treatment room not equipped with the rotating gantry. For example, an irradiation nozzle for irradiating the ion beam to the eye is not installed on the rotating gantry and hence it is not rotated. Such an irradiation nozzle for treating a cancer produced in an eyeball can also be constituted by the irradiation nozzle 18 described above. The ion beam having exited from the synchrotron 4 is similarly introduced to the irradiation nozzle for use in the treatment of the eye.

The energy measuring device 32 used in the above-described embodiment is also applicable to a particle therapy system employing a cyclotron instead of a synchrotron. In the case employing a cyclotron, when the measured energy value exceeds the setting energy value, the interlock device 47 opens a power supply switch for an ion source emitting an ion beam to the cyclotron, and also outputs a shutter closing signal to the shutter controller 48. With the opening of the switch, the emission of the ion beam from the ion source is stopped, whereby the irradiation of the ion beam to the patient 61 is also stopped. The reason why the power supply switch for the ion source is opened is that the cyclotron is not provided with the RF knockout electrode.

What is claimed is:

1. A method of irradiating a charged particle beam comprising the steps of:
   delivering, out of a charged particle beam irradiation apparatus, a charged particle beam which is extracted from a charged particle beam generation apparatus and which arrives at a downstream side of a collimator provided to said charged particle beam irradiation apparatus without being blocked off by said collimator
   introducing a charged particle beam blocked off by said collimator into a plurality of metallic sheets arranged side by side in a direction of advance of the charged particle beam blocked off by said collimator; and
   measuring energy of the charged particle beam blocked off by said collimator based on a position at which the metallic sheet having generated a maximum amount of electric charges is arranged.

2. A method of irradiating a charged particle beam according to claim 1, further comprising:
   stopping extraction of the charged particle beam from said charged particle beam generation apparatus when the measured value of energy of the charged particle exceeds a setting energy value.

3. A method of irradiating a charged particle beam according to claim 1, further comprising the step of attenuating the energy of the charged particle beam blocked off by said collimator before said charged particle beam blocked off by said collimator enters said plurality of metallic sheets.

4. A method of irradiating a charged particle beam according to claim 1, wherein said energy of the charged particle beam blocked off by said collimator is measured by an energy measuring device mounted to said collimator.

5. A method of irradiating a charged particle beam according to claim 4, further comprising the step of stopping extraction of the charged particle beam from said charged particle beam generation apparatus when the measured value of energy of the charged particle exceeds a setting energy value.

6. A method of irradiating a charged particle beam according to claim 4, further comprising the step of attenuating the energy of the charged particle beam blocked off by said collimator before said charged particle beam blocked off by said collimator enters said plurality of metallic sheets.

* * * * *